US009278898B2

(12) United States Patent
Cameretti et al.

(10) Patent No.: US 9,278,898 B2
(45) Date of Patent: Mar. 8, 2016

(54) WORKUP OF A CYCLODODECANONE CYCLODODECANOL MIXTURE IN A DIVIDING WALL COLUMN

(71) Applicants: Luca Cameretti, Dortmund (DE); Daniel Demicoli, Essen (DE); Ralf Meier, Dortmund (DE)

(72) Inventors: Luca Cameretti, Dortmund (DE); Daniel Demicoli, Essen (DE); Ralf Meier, Dortmund (DE)

(73) Assignee: EVONIK DEGUSSA GmbH, Essen (DE)

( * ) Notice: Subject to any disclaimer, the term of this patent is extended or adjusted under 35 U.S.C. 154(b) by 145 days.

(21) Appl. No.: 14/105,237

(22) Filed: Dec. 13, 2013

(65) Prior Publication Data

US 2014/0166470 A1    Jun. 19, 2014

(30) Foreign Application Priority Data

Dec. 17, 2012  (DE) .................... 10 2012 223 367

(51) Int. Cl.
*B01D 3/00*  (2006.01)
*C07C 45/82*  (2006.01)
*B01D 3/14*  (2006.01)

(52) U.S. Cl.
CPC ............... *C07C 45/82* (2013.01); *B01D 3/141* (2013.01)

(58) Field of Classification Search
CPC ............................... B01D 3/141; C07C 45/82
See application file for complete search history.

(56) References Cited

U.S. PATENT DOCUMENTS

| | | | |
|---|---|---|---|
| 2,337,489 A * | 12/1943 | Patterson ................... | 203/81 |
| 3,374,270 A | 3/1968 | Hausen et al. | |
| 3,652,674 A | 3/1972 | Hausen et al. | |
| 4,601,788 A * | 7/1986 | Bannon ..................... | 202/153 |
| 5,200,040 A * | 4/1993 | Naka et al. .................. | 203/25 |
| 6,927,314 B1* | 8/2005 | Schultz et al. ............... | 585/734 |
| 7,267,746 B1* | 9/2007 | Harris et al. ................. | 202/160 |
| 7,431,805 B2* | 10/2008 | Beckman ..................... | 203/2 |
| 7,714,171 B2* | 5/2010 | Pinkos et al. ................ | 568/365 |
| 8,399,658 B2 | 3/2013 | Hengstermann et al. | |
| 2003/0106786 A1 | 6/2003 | Kaibel et al. | |
| 2004/0040829 A1 | 3/2004 | Gall et al. | |
| 2007/0083065 A1 | 4/2007 | Knoesche et al. | |
| 2008/0296145 A1 | 12/2008 | Pinkos et al. | |
| 2009/0288939 A1 | 11/2009 | Smith et al. | |
| 2012/0103013 A1* | 5/2012 | King et al. .................. | 62/625 |
| 2013/0118892 A1 | 5/2013 | Meier et al. | |

FOREIGN PATENT DOCUMENTS

| | | |
|---|---|---|
| DE | 1568317 A1 | 7/1970 |
| DE | 2031782 A1 | 2/1971 |
| DE | 100 21 703 A1 | 11/2001 |

(Continued)

OTHER PUBLICATIONS

Search Report issued on Dec. 23, 2014 in the corresponding European Application No. 13193909.2 (with English Translation of Category of Cited Documents).

*Primary Examiner* — Duane Smith
(74) *Attorney, Agent, or Firm* — Oblon, McClelland, Maier & Neustadt, L.L.P.

(57) ABSTRACT

A process for removing a cyclododecanone-rich fraction from a dehydrogenation mixture containing low boilers, cyclododecanone, medium boilers, cyclododecanol and high boilers is provided. According to the process, the cyclododecanone is separated from the cyclododecanol in a dividing wall column. The apparatus which is the dividing wall column is also provided within this invention.

13 Claims, 4 Drawing Sheets

(56) References Cited

FOREIGN PATENT DOCUMENTS

| | | |
|---|---|---|
| DE | 101 00 552 A1 | 7/2002 |
| DE | 10 2005 048 250 A1 | 4/2007 |
| EP | 2336112 A1 | 6/2011 |
| GB | 930842 | 7/1963 |
| GB | 1 312 086 | 4/1973 |
| JP | 05-000977 A | 1/1993 |
| WO | WO 2005/066113 A1 | 7/2005 |
| WO | WO 2009092682 A2 | 7/2009 |

* cited by examiner

WORKUP OF A CYCLODODECANONE CYCLODODECANOL MIXTURE IN A DIVIDING WALL COLUMN

CROSS REFERENCE TO RELATED APPLICATIONS

This application claims priority to German Application No. 102012223367.9, filed Dec. 17, 2012, the disclosure of which is incorporated herein by reference in its entirety.

BACKGROUND OF THE INVENTION

The invention relates to a process for removing a cyclododecanone-rich fraction from a dehydrogenation mixture comprising low boilers, cyclododecanone, medium boilers, cyclododecanol and high boilers. In the following description, terms and abbreviations as defined in the following paragraphs will be employed.

Butadiene is used hereinafter as a short name for the substance 1,3-butadiene (CAS No. 106-99-0).

CDT is used hereinafter as an abbreviation for 1,5,9-cyclododecatriene (CAS No. 4904-61-4).

CDEN is used hereinafter as an abbreviation for cyclododecene (CAS No. 1501-82-2).

CDAN is used hereinafter as an abbreviation for cyclododecane (CAS No. 294-62-2).

CDON is used hereinafter as an abbreviation for cyclododecanone (CAS No. 830-13-7).

CDOL is used hereinafter as an abbreviation for cyclododecanol (CAS No. 1724-39-6).

CDOL t.q. stands for CDOL in technical-grade quality and refers to a mixture containing 75 to 85% by weight of CDOL and 10 to 20% by weight of CDON.

Oxime is used hereinafter as a short name for the oxime of CDON (CAS No. 9466-89-4).

Laurolactam is a common name for azacyclotridecan-2-one (CAS No. 947-04-6).

Laurolactam is the starting material of the production of the high-performance polymer nylon-12. Laurolactam may be obtained on the industrial scale via the following route: butadiene, which is obtained in mineral oil processing, may be converted by catalytic cyclotrimerization to CDT. Hydrogenation of CDT gives CDAN. Oxidation of CDAN with (atmospheric) oxygen results in a mixture of CDOL and CDON. This mixture is subjected to a dehydrogenation which converts the CDOL present in the mixture to CDON. A dehydrogenation mixture comprising principally CDON is obtained. In addition, the dehydrogenation mixture comprises unconverted CDOL and further components. High-purity CDON is separated from the dehydrogenation mixture. The high-purity CDON is oximated to its oxime. The oxime may subsequently be reacted with sulphuric acid to give laurolactam.

The overall process is described in greater detail in Oenbrink, G. and Schiffer, T. 2009. Cyclododecanol, Cyclododecanone, and Laurolactam. Ullmann's Encyclopedia of Industrial Chemistry. DOI: 10.1002/14356007.a08_201.pub2.

The present invention addresses the problem of workup of the CDON/CDOL-containing dehydrogenation mixture with the aim to obtain high-purity CDON.

The dehydrogenation mixture obtained by the route described above comprises, as well as CDON and CDOL, further components in the form of low boilers, medium boilers and high boilers.

"Low boilers" in the context of this invention are substances or substance mixtures which have a lower boiling point than CDON under the same pressure conditions and are therefore enriched in the distillate in the course of distillative separation of a mixture of low boilers and CDON. The significant low boilers in this connection include: cyclododecene (CDEN), cyclododecane (CDAN), dodecanal, and cyclododecane epoxide. Cyclododecane epoxide is at the limit of the above definition of the low boilers, since its boiling point of about 150° C. at 40 mbar corresponds virtually to that of CDON and it is therefore virtually inseparable in an economically viable manner from the CDON. Smaller amounts (less than 100 ppm) of the low boilers acetic acid and decane may also be present, but these are barely of any relevance for the separation tasks.

"Medium boilers" in the context of this invention are substances or substance mixtures which, under the same pressure conditions, have a higher boiling point than CDON and a lower boiling point than CDOL, and are therefore enriched in the middle of the column in the course of distillative separation of a mixture of CDON, medium boilers and CDOL. A medium boiler in this connection is particularly dodecan-1-ol. The fraction of the medium boilers may include further organic substances which have not been fully characterized to date.

"High boilers" in the context of this invention are substances or substance mixtures which, under the same pressure conditions, have a higher boiling point than CDOL and therefore remain in the residue in the distillative separation of a mixture of high boilers and CDOL. The high boiler limit is at about 180° C. and a pressure of 46 mbar. The high boilers include especially cyclododecanediol. In addition, the fraction of the high boilers comprises further organic substances which have not been characterized specifically to date.

The dehydrogenation of CDOL to CDON is described in DE1568317 and DE1248650. These describe dehydrogenation mixtures containing 74 to 89% by weight of CDON and 25.9 to 21.8% by weight of CDOL. The remaining fraction of the dehydrogenation mixture prepared is accounted for by low boilers and medium boilers. The workup of the dehydrogenation mixture is not described any further.

Japanese patent application JP05-000977A discloses a process for preparing high-purity CDOL from a CDON/CDOL mixture. During the distillative workup of the mixture, a small proportion of alkaline components is added to the mixture to be separated. A dividing wall column is not utilized for workup of the mixture.

The oxidation of CDAN to an oxidation mixture comprising CDAN and CDOL is described in GB930842. The processing steps according to the present invention are not disclosed.

DE2031782 describes a process for selective preparation of CDON, in which CDAN is oxidized in order to obtain a mixture of CDON and CDOL. The mixture is worked up by distillation, but without more specific description of the distillation operation.

WO2009/092682 discloses a process for workup of a CDON/CDOL-containing mixture, which is worked up with the aid of a dividing wall column. In this process, however, the medium boiler is the main component of the feed, while the low and high boilers are unwanted by-products.

The processing of a laurolactam-containing mixture in a dividing wall column is mentioned in EP2336112A1. According to the process described, the feed to the dividing wall column consists predominantly of medium boilers.

The CDON used for the preparation of laurolactam should be present in a form of maximum purity, since accompanying components cause lasting damage to the polymers in the nylon-12. These secondary components arise particularly during the oxidation of the CDAN and also during the dehydrogenation of the CDOL.

Therefore, there is a need for a process for workup of a mixture comprising low boilers, CDON, medium boilers, CDOL and high boilers, in which a fraction consisting of CDON of maximum purity is obtained. The plant for performance of this process should entail a minimum level of capital costs.

SUMMARY OF THE INVENTION

These objectives and others are met by the present invention, the first embodiment of which includes a process for removing a cyclododecanone-rich fraction (A) from a dehydrogenation mixture (O), the dehydrogenation mixture (O) comprising: low boilers (LB); cyclododecanone (CDON); medium boilers (MB); cyclododecanol (CDOL) and high boilers (HB); the process comprising:

a) feeding the dehydrogenation mixture (O) to a preliminary separator column;

b) distillatively removing the low boilers (LB) from the dehydrogenation mixture (O) to obtain a first mixture (ABC1) comprising cyclododecanone (CDON), medium boilers (MB), cyclododecanol (CDOL) and high boilers (HB);

c) feeding the first mixture (ABC1) into a dividing wall column (DWC), which comprises:
  a left-hand column section (LHS);
  a right-hand column section (RHS),
  a dividing wall (W) which separates the left-hand column section (LHS) and the right-hand column section (RHS) and extends along the dividing wall column (DWC) such that a top (7) and a bottom (8) of the two column sections (LHS, RHS) are combined, and
  a permeable connection (V) between the two column sections (LHS, RHS) which bypasses the dividing wall (W) at a separation stage disposed between the top (7) and bottom (8);

d) drawing off the cyclododecanone-rich fraction (A) from the top (7) of the dividing wall column (DWC);

e) drawing off a second mixture (ABC2) comprising cyclododecanone (CDON), cyclododecanol (CDOL) and medium boilers (MB) from a side draw (S) of the dividing wall column (DWC);

f) drawing off a fraction (C) comprising cyclododecanol (CDOL) and high boilers (HB) from the bottom (8) of the dividing wall column (DWC).

In another embodiment, the present invention includes an apparatus for the distillative workup of substance mixtures, comprising:

a space which is surrounded by a shell (9) and is divided into a left-hand column section (LHS), a right-hand column section (RHS), a bottom (8) and a top (7), a dividing wall (W) which separates the left-hand column section (LHS) from the right-hand column section (RHS) extends through the shell (9) between the bottom (8) and top (7), a feed for the introduction of a substance mixture (ABC1), a draw at the top for the removal of a first fraction (A), a draw at the bottom for the removal of a second fraction (C);

a side draw (S) for the removal of a third fraction (ABC2); and a permeable connection (V) between the two column sections (LHS, RHS) arranged between the top (7) and bottom (8).

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE PREFERRED EMBODIMENTS

Figure 1:
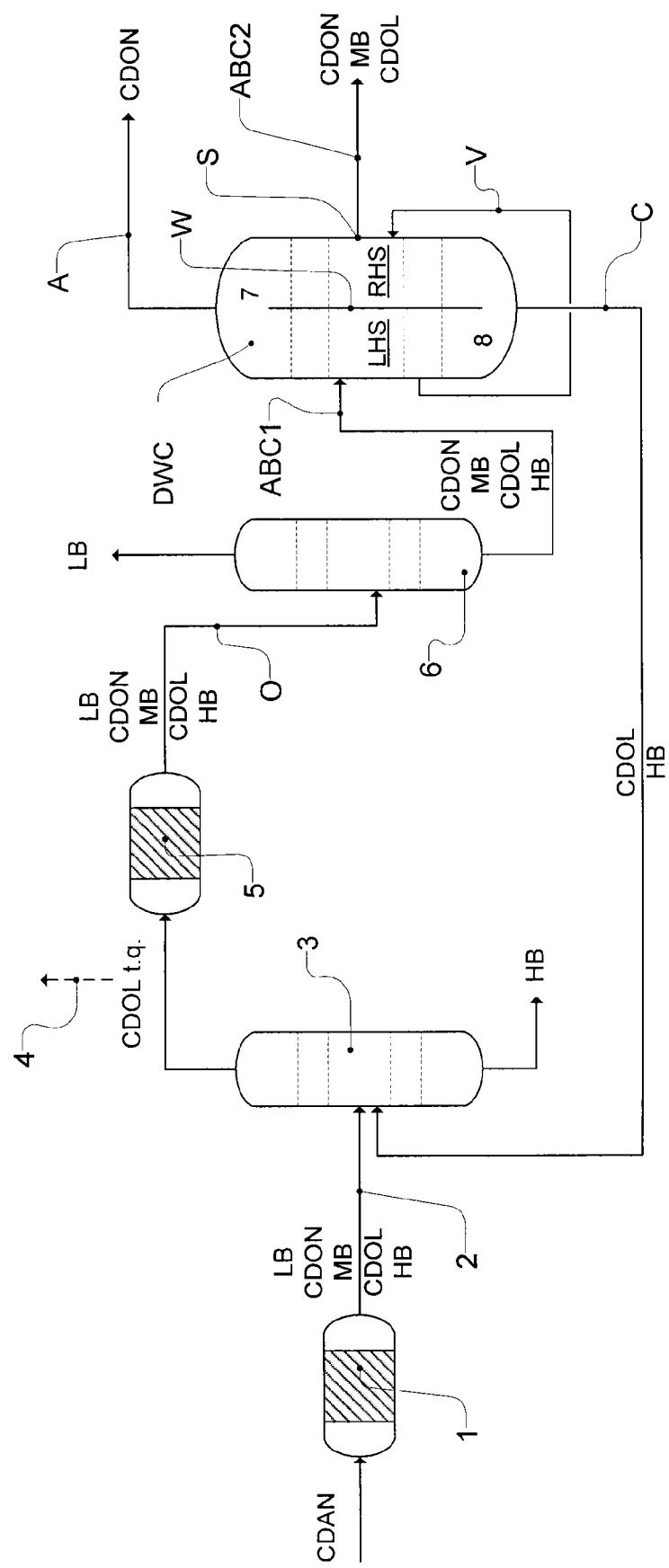
FIG. 1 shows a process flow diagram according to an embodiment of the present invention.

Throughout this description all ranges described include all values and sub-ranges therein, unless otherwise specified.

Additionally, the indefinite article "a" or "an" carries the meaning of "one or more" throughout the description, unless otherwise specified.

In a first embodiment, the present invention provides a process for removing a cyclododecanone-rich fraction (A) from a dehydrogenation mixture (O), the dehydrogenation mixture (O) comprising: low boilers (LB); cyclododecanone (CDON); medium boilers (MB); cyclododecanol (CDOL) and high boilers (HB); the process comprising:

a) feeding the dehydrogenation mixture (O) to a preliminary separator column;

b) distillatively removing the low boilers (LB) from the dehydrogenation mixture (O) to obtain a first mixture (ABC1) comprising cyclododecanone (CDON), medium boilers (MB), cyclododecanol (CDOL) and high boilers (HB);

c) feeding the first mixture (ABC1) into a dividing wall column (DWC), which comprises:
  a left-hand column section (LHS);
  a right-hand column section (RHS),
  a dividing wall (W) which separates the left-hand column section (LHS) and the right-hand column section (RHS) and extends along the dividing wall column (DWC) such that a top (7) and a bottom (8) of the two column sections (LHS, RHS) are combined, and
  a permeable connection (V) between the two column sections (LHS, RHS) which bypasses the dividing wall (W) at a separation stage disposed between the top (7) and bottom (8);

d) drawing off the cyclododecanone-rich fraction (A) from the top (7) of the dividing wall column (DWC);

e) drawing off a second mixture (ABC2) comprising cyclododecanone (CDON), cyclododecanol (CDOL) and medium boilers (MB) from a side draw (S) of the dividing wall column (DWC);

f) drawing off a fraction (C) comprising cyclododecanol (CDOL) and high boilers (HB) from the bottom (8) of the dividing wall column (DWC).

The invention therefore provides a process for removing a cyclododecanone-rich fraction from a dehydrogenation mixture comprising low boilers, cyclododecanone, medium boilers, cyclododecanol and high boilers, which comprises: a) providing the dehydrogenation mixture; b) distillatively removing the low boilers from the dehydrogenation mixture to obtain a first mixture comprising cyclododecanone, medium boilers, cyclododecanol and high boilers; c) feeding the first mixture into a dividing wall column having a left-hand column section and a right-hand column section, in which the two column sections are partly divided by a dividing wall which extends along the dividing wall column such that the top and bottom of the two column sections are combined, and in which a permeable connection between the two column sections which bypasses the dividing wall is provided at a separation stage disposed between the top and bottom; d) drawing off the cyclododecanone-rich fraction from the top of the dividing wall column; e) drawing off a second mixture comprising cyclododecanone, cyclododecanol and medium boilers from a side draw of the dividing wall column; f) drawing off a fraction comprising cyclododecanol and high boilers from the bottom of the dividing wall column.

An element of the present invention is the use of a "holed" dividing wall column having a permeable connection between the two column sections. The term "hole" in this connection should not be understood in such a way that the dividing wall necessarily has an orifice. Instead, the term "hole" should be understood in the figurative sense, as a connection between the two column sections which allows mass transfer from a point in one column section to the other, which is otherwise prevented by the dividing wall.

Because of this connection, the holed dividing wall column constitutes an integrated construction of two series-connected side draw columns with combined tops and bottoms. The advantage of this combination is the possibility of dispensing with one condenser and one vaporizer overall, such that the holed dividing wall column entails lower capital costs than an equivalent combination of two individual columns. The comparison between the inventive dividing wall column with a "hole" and an arrangement of two sidestream columns with combined top and bottom streams, which is equivalent for separation purposes but more costly, is illustrated in detail by FIGS. 3 and 4.

In a preferred embodiment of the invention, the first mixture is fed into the left-hand column section of the dividing wall column and the second mixture is drawn off in the right-hand column section from a side draw therein. The connection therefore constitutes a withdrawal on the feed side and an additional feed on the withdrawal side.

In a further preferred embodiment of the invention, the permeable connection may be designed to transport liquid medium boilers between the two column sections. The connection in this case constitutes a liquid connection between the two column sections.

In order to ensure that exclusively liquid substances switch column sides via the permeable connection, the connection should originate at a liquid collector in the left-hand column section. Liquid collectors are known in distillation technology and serve primarily to collect the liquid flowing away from a bed of structured or random packing and to apply it to a liquid distributor which distributes the liquid homogeneously over a bed below. Optionally, a portion of the collected liquid may be withdrawn as a side draw. The connection between the two column sections may thus be conventionally drawn off as a side stream on the left and applied like a feed on the right. The requirement that exclusively a liquid stream is exchanged between the two column sections is also a reason why the inventive dividing wall column does not necessarily have a hole in the dividing wall, since a simple hole is also permeable to gaseous media.

In a very particularly preferred embodiment of the invention, the permeable connection is positioned such that it originates at the separation plane of the left-hand column section at which the liquid concentration of the medium boilers in the left-hand column section is at a maximum, and such that the permeable connection opens at the separation plane of the right-hand column section at which the composition of the liquid phase corresponds as far as possible to that of the liquid stream withdrawn from the left-hand column section. This means that, in the left-hand section of the dividing wall column, the medium boilers are concentrated to a few percent and tapped off at the concentration peak, and this stream is fed back in again on the right-hand side via the connection. On the right-hand side, the column may then be operated with an increased reflux ratio, such that the medium boilers can be concentrated to high values of up to 40% and withdrawn in the side stream.

Preferably, the dividing wall column may be run under reduced pressure, i.e. at a pressure below 1 bar absolute. More particularly, the pressure within the dividing wall column may be below 50 mbar absolute.

The diameter ratio of the right-hand column section to the left-hand column section and the number of any internals in the two column sections may be selected such that the desired flow conditions are established in the two column sections, taking account of the equivalence of the hydraulic resistance for gases.

In one embodiment, the process according to the invention serves for workup of a dehydrogenation mixture having the following composition which adds up to 100%:
Low boilers (LB): 1 to 8% by weight, preferably 3% by weight;
Cyclododecanone (CDON): 60 to 90% by weight, preferably 70% by weight;
Medium boilers (MB): 0 to 1.5% by weight, preferably 1% by weight;
Cyclododecanol (CDOL): 10 to 40% by weight, preferably 24% by weight;
High boilers (HB): 0.1 to 2.5% by weight, preferably 2% by weight.

The process preferably serves to obtain a cyclododecanone-rich fraction having a particularly high purity. According to the invention, this fraction should have a CDON content of at least 98%, preferably even a target CDON content of 99.5% by weight. In addition, the cyclododecanone-rich fraction drawn off at the top of the dividing wall column should as far as possible be free of CDOL, high boilers and medium boilers. The fraction drawn off at the bottom of the dividing wall column may accordingly be very substantially free of CDON.

If the process according to the invention is used in the course of a laurolactam process, the step of "providing the dehydrogenation mixture" may comprise the following components:
g) oxidation of cyclododecane with oxygen to obtain an oxidation mixture comprising low boilers, cyclododecanone, medium boilers, cyclododecanol and high boilers;
h) distillatively removing a cyclododecanol-rich fraction from the oxidation mixture, said fraction having been depleted of high boilers;
i) dehydrogenating the cyclododecanol-rich fraction to obtain the dehydrogenation mixture.

If the process according to the invention is part of a laurolactam process, it is advisable to recycle the bottoms from the dividing wall column into step h). This is because this bottom fraction comprises a large portion of CDOL, which can be made available again to the dehydrogenation operation and converted to CDON in this way. The high boilers are concentrated up to a limiting concentration and are circulated there-with. The high boilers newly introduced into the process via the oxidation leave the process again via the bottom of the preliminary separator column and via the side draw of the dividing wall column.

The top product of the dividing wall column is high-purity CDON, which is of excellent suitability to be oximated and then processed further to give laurolactam. The second mixture provided by the dividing wall column can either be worked up further in order to obtain pure CDON and/or CDOL (for example by batch distillation) or utilized thermally. In the simplest case, the latter may be accomplished by combustion. The tangible heat can optionally be tapped off beforehand.

The invention also provides the dividing wall column used in the process as such. This is an apparatus for the distillative workup of substance mixtures into three fractions, comprising a space which is surrounded by a shell and is divided into a left-hand column section, a right-hand column section, a bottom and a top, in which a dividing wall which separates the left-hand column section from the right-hand column section extends through the dividing wall column within the shell between the bottom and top, and in which a feed for the introduction of the substance mixture, a draw at the top for the removal of the first fraction, a draw at the bottom for the removal of the second fraction and a side draw for the removal of the third fraction are provided, and in which a permeable connection between the two column sections is disposed between the top and bottom. The inventive apparatus thus has a combined top and a combined bottom.

Thus in one particular embodiment, the present invention provides an apparatus for the distillative workup of substance mixtures, comprising:

a space which is surrounded by a shell (9) and is divided into a left-hand column section (LHS), a right-hand column section (RHS), a bottom (8) and a top (7), a dividing wall (W) which separates the left-hand column section (LHS) from the right-hand column section (RHS) extends through the shell (9) between the bottom (8) and top (7), a feed for the introduction of a substance mixture (ABC1), a draw at the top for the removal of a first fraction (A), a draw at the bottom for the removal of a second fraction (C);

a side draw (S) for the removal of a third fraction (ABC2); and a permeable connection (V) between the two column sections (LHS, RHS) arranged between the top (7) and bottom (8).

The permeable connection between the two column sections may preferably be disposed outside the shell of the apparatus. The connection is preferably a draw from the left-hand side and a feed for the right-hand side.

Further advantageous features of this apparatus are apparent from the description and the examples.

The invention further provides for the use of this apparatus for workup of a substance mixture comprising low boilers, CDON, medium boilers, CDOL and high boilers.

Having generally described this invention, a further understanding can be obtained by reference to certain specific examples which are provided herein for purposes of illustration only and are not intended to be limiting unless otherwise specified.

The overall workup operation is shown in FIG. 1. It commences in an oxidation 1 in which CDAN is oxidized with oxygen. This gives an oxidation mixture 2 comprising low boilers LB, CDON, medium boilers MB, CDOL and high boilers HB. On the basis of the reaction mechanism, the CDON content within the oxidation mixture 2 is much lower than the CDOL content. Typically, such an oxidation mixture 2 contains about 15% by weight of CDON and about 70% by weight of CDOL.

The oxidation mixture 2 is fed into a preliminary separator column 3. The function of this preliminary separator column 3 is to discharge a large proportion of the high boilers HB. This is done via the bottom. CDOL t.q. is drawn off via the top of the preliminary separator column 3. CDOL t.q. contains about 84% by weight of CDOL and 13% by weight of CDON. CDOL t.q. constitutes a separate saleable product and can optionally be discharged from the process via a branch 4.

For the laurolactam preparation, CDOL t.q. is subjected to a dehydrogenation 5. This dehydrogenates CDOL to CDON, such that the proportion of these two substances is reversed. The dehydrogenation mixture O drawn off from the dehydrogenation 5 typically has the following composition which adds up to 100%:

Low boilers (LB): 1 to 8% by weight, preferably 3% by weight;
Cyclododecanone (CDON): 60 to 90% by weight, preferably 70% by weight;
Medium boilers (MB): 0 to 1.5% by weight, preferably 1% by weight;
Cyclododecanol (CDOL): 10 to 40% by weight, preferably 24% by weight;
High boilers (HB): 0.1 to 2.5% by weight, preferably 2% by weight.

The dehydrogenation mixture O is then fed into a low boiler column 6. The purpose of the low boiler column 6 is to remove the low boilers LB by overhead distillation out of the dehydrogenation mixture O, such that a first mixture ABC1 comprising CDON, medium boilers MB, CDOL and high boilers HB is obtained at the bottom of the low boiler column 6. The low boilers LB are preferably removed completely in this step. The special feature of the bottom product ABC1 is that its content of medium boilers MB is extremely low, namely only about 1% by weight. For the rest, the mixture ABC1 consists essentially of CDON, CDOL and high boilers HB. A typical composition of the mixture ABC1 is as follows:

Low boilers (LB): 0 to 1% by weight, preferably 0% by weight;
Cyclododecanone (CDON): 60 to 90% by weight, preferably 70% by weight;
Medium boilers (MB): 0 to 2% by weight, preferably 1% by weight;
Cyclododecanol (CDOL): 10 to 40% by weight, preferably 26% by weight;
High boilers (HB): 0.1 to 3% by weight, preferably 3% by weight.

Mixture ABC1 is then fed into a dividing wall column DWC. The dividing wall column DWC comprises a dividing wall W which separates a left-hand section of the dividing wall column LHS from a right-hand section of the dividing wall column RHS. The top 7 and bottom 8 of the dividing wall column are combined. In a separation plane between the top 7 and bottom 8, there is a connection V between the two halves of the dividing wall column LHS and RHS. The connection V thus constitutes a draw from the left-hand side and a feed for the right-hand side. On the right-hand side of the dividing wall column RHS, a side draw S is also provided. The specific construction of the dividing wall column DWC is apparent from FIG. 2.

From the top 7 of the dividing wall column DWC, a CDON-rich fraction A consisting to an extent of 99.5% of CDON is drawn off From the bottom 8 of the dividing wall column DWC, a fraction C comprising CDOL and high boilers HB is drawn off. This bottom fraction C is recycled and conducted together with the oxidation mixture 2 into the preliminary separator column 3. In this way, the unconverted CDOL is fed back to the dehydrogenation 5. The recycled high boilers HB are concentrated to a certain degree in the process. The high boilers HB freshly introduced from the oxidation 1 are separated out via the bottom of the preliminary separator column 3, such that a steady state is established with regard to the high boiler concentration.

Through the side draw S, a second mixture ABC2 is drawn off, comprising CDON, CDOL and medium boilers. The medium boilers MB constitute the greatest proportion of the side mixture ABC2. The proportion of the product of value CDON and CDOL is lower. Mixture ABC2 can be purified further, for example, by batch distillation or sent to a thermal utilization. The high-purity CDON in fraction A drawn off from the top 7 of the dividing wall column DWC is used for laurolactam preparation (not shown).

Figure 2:
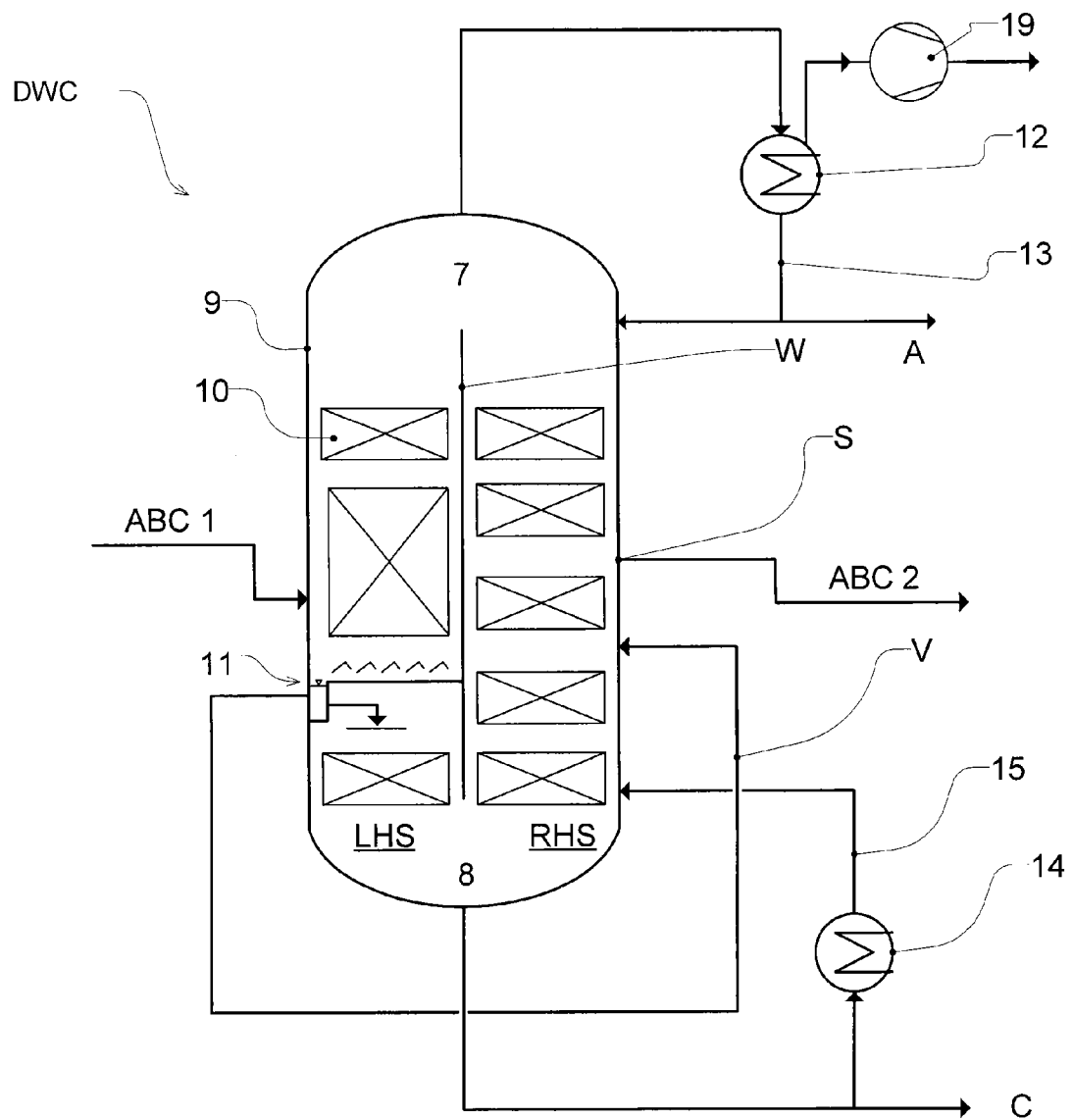
FIG. 2 shows a schematic diagram of a dividing wall column according to an embodiment of the present invention.

A schematic structure of a dividing wall column DWC is shown in detail in FIG. 2. The dividing wall column DWC comprises a shell 9 which surrounds an inner space. The space is divided into a left-hand column section LHS, a right-hand column section RHS, a top 7 and a bottom 8. A wall W which extends through the dividing wall column DWC within the shell 9 physically separates the left-hand column section from the right-hand column section. In the top 7 and at the bottom 8, the two column sections are physically combined, since the dividing wall W does not extend over the entire height of the dividing wall column DWC. The top 7 and bottom 8 commence where the dividing wall W stops.

A multitude of internals 10 known per se may be incorporated into the dividing wall column DWC, for example structured packings or random packings from Sulzer or Montz. The purpose of the internals 10 is to achieve a maximum number of theoretical plates.

In addition, various liquid collectors and distributors 11 may be provided in the dividing wall column DWC, and are of designs customary in the art.

An essential feature of the dividing wall column DWC used in accordance with the invention is a permeable connection V from the left-hand column side LHS to the right-hand column side RHS. The connection V is a liquid conduit provided with a circulation pump, which is not shown, to establish a flow through the conduit. By means of the connection V, a liquid medium boiler is transferred from the concentration maximum thereof on the left-hand side to the right-hand side of the column; in this regard, see also explanation for FIG. 4. In order to ensure that exclusively liquid substances are exchanged via the connection V, the connection V originates from a liquid collector 11 on the left-hand side. The liquid collector 11 is installed at a separation plane at which the liquid concentration of the medium boilers has a maximum. The permeable connection thus originates at the separation plane of the left-hand column section at which the liquid concentration in the medium boiler in the left-hand column section is at a maximum. The permeable connection V opens out at the separation plane of the right-hand column section at which the composition of the liquid phase corresponds as far as possible to that of the liquid stream withdrawn from the left-hand column section. This means that the medium boiler is concentrated to a few percent in the left-hand section of the dividing wall column and tapped off at the concentration peak, and this stream is fed back via the connection on the right-hand side. The draw and feed points for the connection V are accordingly selected in accordance with the concentration ratios and need not be on the same plane.

The stream transported via the connection V may have the following composition which adds up to 100%:
Cyclododecanone (CDON): 30 to 50% by weight, preferably 43% by weight;
Medium boilers (MB): 0 to 20% by weight, preferably 18% by weight;
Cyclododecanol (CDOL): 30 to 50% by weight, preferably 38.4% by weight;
High boilers (HB): 0.1 to 2% by weight, preferably 0.6% by weight.

From the top 7 of the dividing wall column, a gaseous top product A is drawn off, which comprises almost exclusively CDON (approx. 99.5% by weight). As usual in distillation columns, a condenser 12 and a tops reflux 13 are provided at the top draw. Also disposed at the top is a vacuum system 19 which generates a reduced pressure in the dividing wall column DWC.

At the bottom 8 of the dividing wall column DWC, a fraction C is drawn off, comprising predominantly CDOL and high boilers. As usual in distillation columns, a reboiler/vaporizer 14 is provided here with the corresponding bottoms reflux 15.

On the right-hand side of the dividing wall column RHS is provided a side draw S through which a second mixture ABC2 rich in medium boilers is drawn off. The mixture ABC2 drawn off from the side draw comprises essentially CDON, CDOL and medium boilers.

The stream ABC2 withdrawn via the side draw may have the following composition which adds up to 100%:
Cyclododecanone (CDON): 20 to 50% by weight, preferably 35% by weight;
Medium boilers (MB): 0 to 60% by weight, preferably 54% by weight;
Cyclododecanol (CDOL): 10 to 50% by weight, preferably 10% by weight;
High boilers (HB): 0 to 2% by weight, preferably 1% by weight.

Figure 3:
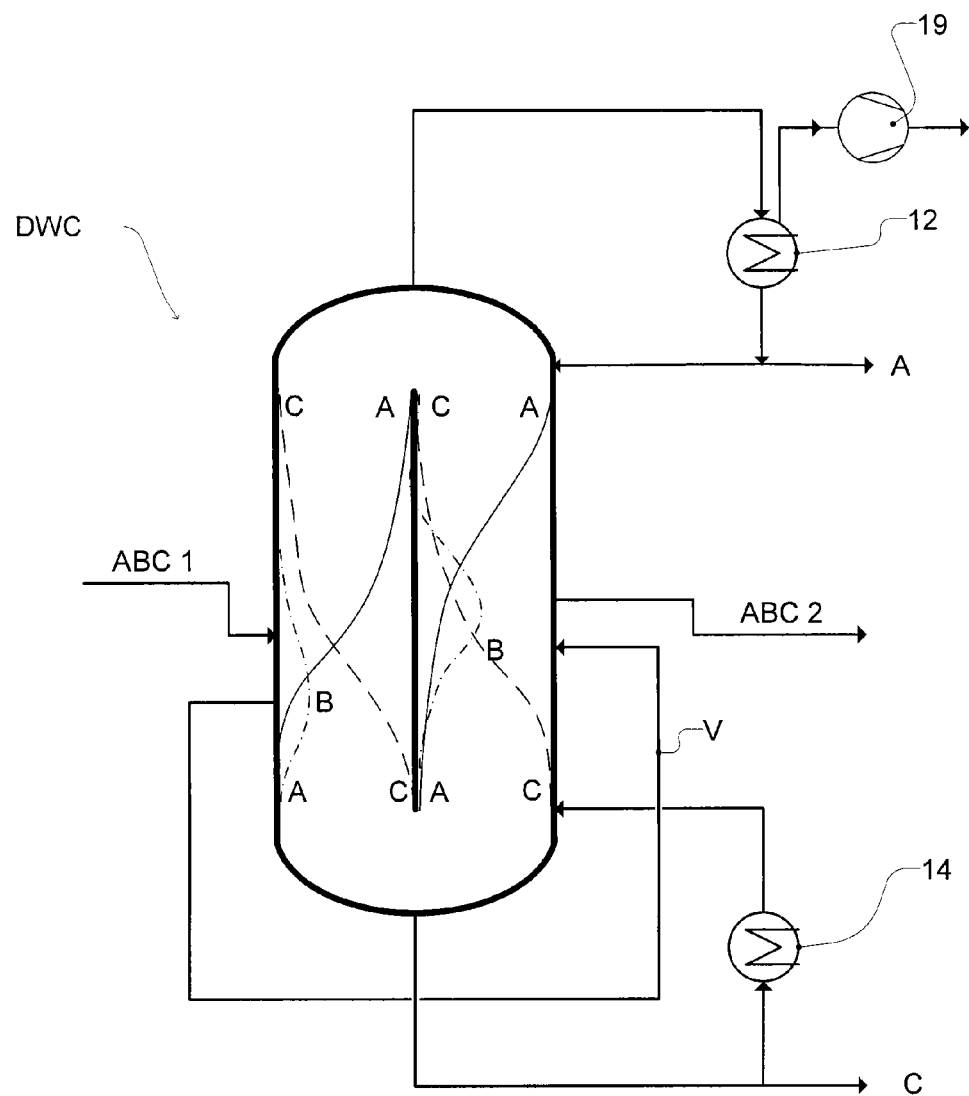
FIG. 3 shows concentration profiles of mixture components within a dividing wall column according to an embodiment of the present invention.

FIG. 3 is another drawing of the dividing wall column, but now with the concentration profiles of CDON (solid line, fraction A), CDOL (broken line, fraction C) and medium boilers (line of dashes and dots, fraction B). The connection V is arranged such that it originates at the separation plane of the left-hand column section at which the liquid concentration in the medium boiler in the left-hand column section is at a maximum. The connection opens out at the separation plane of the right-hand column section at which the composition of the liquid phase corresponds as far as possible to that of the liquid stream withdrawn from the left-hand column section. This means that the medium boiler is concentrated to a few percent in the left-hand section of the dividing wall column and tapped off at the concentration peak, and this stream is fed back via the connection on the right-hand side. In this way, the mixture ABC1 is separated in the left-hand column such that CDON is obtained as a pure distillate and CDOL as a pure high boiler. The medium boiler forms a concentration peak within the left-hand section of the dividing wall column. At the point of the concentration maximum, a substream of liquid medium boiler is withdrawn and transferred via the connection V into the right-hand section of the dividing wall column. A sharp separation of CDON and CDOL is again conducted there with elevated reflux. The medium boiler is in turn highly concentrated within the right-hand section of the dividing wall column and can be removed via the side stream S. Since the distillates of the two column sections and the bottoms of the two column sections each have the same concentration (pure products), they can be combined and run through one condensation system 12, one vacuum system 19 and one vaporizer 14.

Figure 4:
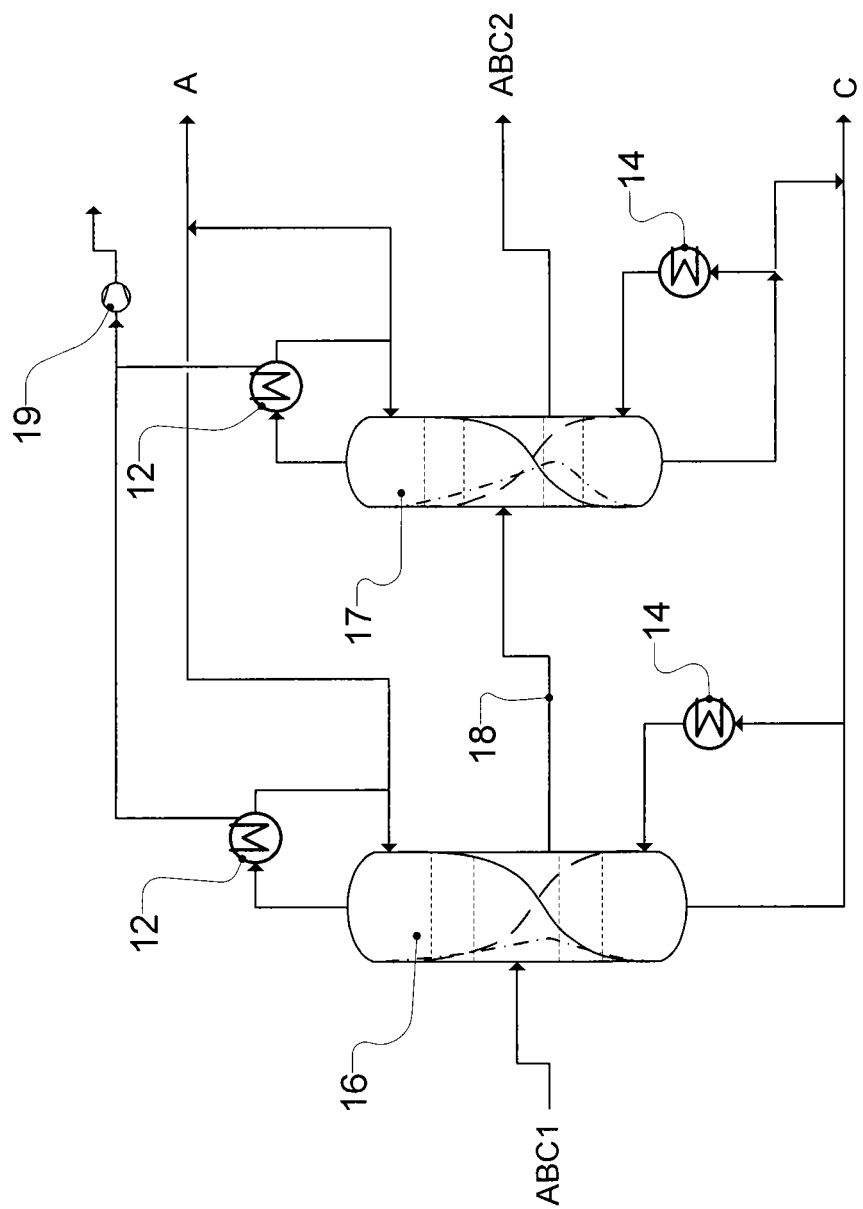
FIG. 4 shows a conventional apparatus set which would be equivalent to the dividing wall column according to an embodiment of the present invention.

An equivalent solution for separation purposes is shown in FIG. 4: no dividing wall column is employed here; instead, two conventional side draw columns 16 and 17 are connected in series. The first column 16 corresponds to the left-hand section of the dividing wall column, the second section 17 to the right-hand section of the dividing wall column. The function of the connection V is adopted by a side stream 18 between the first column 16 and the second column 17. The bottoms and distillates of the two columns 17 and 18 are combined to give common fractions A and C. The concentration profiles in the two columns 16 and 17 are selected, respectively, as in the left-hand and right-hand sections of the dividing wall column (see FIG. 3). In this way, the same separation result may be achieved. However, the plant shown in FIG. 4 requires greater capital costs, since each of the two columns 16 and 17 requires an individual vaporizer 14 and condenser 12. Since the dividing wall column shown in FIG. 3 requires only one vaporizer and one condenser, the inventive execution shown in FIG. 3 is much less expensive.

Numerous modifications and variations on the present invention are possible in light of the above description. It is therefore to be understood that within the scope of the following Claims, the invention may be practiced otherwise than as specifically described herein. Any such embodiments are intended to be within the scope of the present invention.

LIST OF REFERENCE NUMERALS

1 Oxidation
2 Oxidation mixture
3 Preliminary separator column
4 Branch
5 Dehydrogenation
6 Low boiler column
7 Top of dividing wall column
8 Bottom of dividing wall column
9 Shell
10 Column internals
11 Liquid collector
12 Condenser
13 Tops reflux
14 Reboiler/vaporizer
15 Bottoms reflux
16 First column
17 Second column
18 Side stream
19 Vacuum system
LB Low boilers
MB Medium boilers
HB High boilers
DWC Dividing wall column
RHS Right-hand section of the dividing wall column
LHS Left-hand section of the dividing wall column
W Dividing wall
V Connection
S Side draw
O Dehydrogenation mixture
A CDON-rich fraction (tops of dividing wall column)
B Medium boiler-rich fraction (connection of dividing wall column sides)
C CDON/high boiler-containing fraction (bottoms of dividing wall column)
ABC1 First mixture (feed of dividing wall column)
ABC2 Second mixture (side draw of dividing wall column)

The invention claimed is:

1. A process for removing a cyclododecanone-rich fraction (A) from a dehydrogenation mixture (O), the dehydrogenation mixture (O) comprising:
 components having a boiling point less than cyclododecanone (CDON) (LB); cyclododecanone (CDON);
 components having a boiling point between CDON and cyclododecanol (CDOL) (MB);
 cyclododecanol (CDOL); and
 components having a boiling point above CDOL (HB);
 the process comprising:
 a) feeding the dehydrogenation mixture (O) to a preliminary separator column;
 b) distillatively removing the LB components from the dehydrogenation mixture (O) to obtain a first mixture (ABC1) comprising the cyclododecanone (CDON), the MB components, the cyclododecanol (CDOL) and the HB components;
 c) feeding the first mixture (ABC1) into a dividing wall column (DWC), which comprises:
 a left-hand column section (LHS);
 a right-hand column section (RHS),
 a dividing wall (W) which separates the left-hand column section (LHS) and the right-hand column section (RHS) and extends along the dividing wall column (DWC) such that a top (7) and a bottom (8) of the two column sections (LHS, RHS) are combined, and
 a liquid connection (V) between the two column sections (LHS, RHS) which bypasses the dividing wall (W) and is located at a separation stage disposed between the top (7) and bottom (8);
 d) drawing off the cyclododecanone-rich fraction (A) from the top (7) of the dividing wall column (DWC);
 e) drawing off a second mixture (ABC2) comprising cyclododecanone (CDON), cyclododecanol (CDOL) and the MB components from a side draw (S) of the dividing wall column (DWC);
 f) drawing off a fraction (C) comprising cyclododecanol (CDOL) and the HB components from the bottom (8) of the dividing wall column (DWC).

2. The process according to claim 1, wherein
 the first mixture (ABC1) is fed into the left-hand column section (LHS), and
 the second mixture (ABC2) is drawn off from the side draw (S) present in the right-hand column section (RHS).

3. The process according to claim 2, wherein the liquid connection (V) between the LHS and RHS column sections transports liquid comprising MB components from the left-hand column section (LHS) to the right-hand column section (RHS).

4. The process according to claim 3, wherein the LHS comprises a liquid collector and the liquid connection (V) originates at the liquid collector.

5. The process according to claim 3, wherein
 the liquid connection (V) originates at a separation plane of the left-hand column section (LHS) having a maximum concentration of the MB components, and
 the liquid connection (V) opens at a separation plane of the right-hand column section (RHS) having a MB component composition corresponding to the MB components concentration of the left-hand column.

6. The process according to claim 1, wherein a pressure of the dividing wall column (DWC) is below 1 bar absolute.

7. The process according to claim 1, wherein the dehydrogenation mixture (O) comprises:
 LB components: 1 to 8% by weight;
 Cyclododecanone (CDON): 60 to 90% by weight;

MB components: 0 to 1.5% by weight;
Cyclododecanol (CDOL): 10 to 40% by weight;
HB components: 0.1 to 2.5% by weight;
wherein a sum of the weight % values is 100%.

8. The process according to claim 1, wherein a content of cyclododecanone (CDON) in the cyclododecanone-rich fraction (A) is at least 98% by weight.

9. The process according to claim 1, wherein the fraction (C) comprising cyclododecanol (CDOL) and HB components is free of cyclododecanone (CDON).

10. The process according to claim 1, wherein the dehydrogenation mixture (O) is obtained by a process comprising:
   g) oxidation of cyclododecane (CDAN) with oxygen to obtain an oxidation mixture (2) comprising the LB components, cyclododecanone (CDON), the MB components, cyclododecanol (CDOL) and the HB components
   h) distillatively removing a cyclododecanol-rich fraction (CBOL technical quality) (CDOL t.q.) from the oxidation mixture (2);
   i) removing the HB components from the CDOL t.q. to obtain a fraction (C) comprising cyclododecanol (CDOL) and high boilers (HB);
   removing the HB components from the CDOL to obtain a cyclododecanol-rich fraction; and
   j) dehydrogenating the cyclododecanol-rich fraction from which the high boilers are removed to obtain the dehydrogenation mixture (O).

11. The process according to claim 10, wherein the fraction (C) comprising cyclododecanol (CDOL) and the HB components is recycled into h).

12. The process according to claim 1, further comprising:
   oximating the cyclododecanone-rich fraction (A) to obtain an oxime of cyclododecanone; and
   reacting the cyclododecane oxime with sulfuric acid to obtain laurolactam.

13. A dividing wall column for the process of claim 1, comprising:
   a space which is surrounded by a shell (9) and is divided into a left-hand column section (LHS), a right-hand column section (RHS), a bottom (8) and a top (7),
   a dividing wall (W) which separates the left-hand column section (LHS) from the right-hand column section (RHS) and extends through the shell (9) between the bottom (8) and top (7),
   a feed for the introduction of the first mixture (ABC1),
   a draw at the top for the removal of the CDON fraction (A),
   a draw at the bottom for the removal of the CDOL fraction (C);
   a side draw (S) for the removal of ABC2 fraction; and
   a liquid connection (V) between the LHS and RHS column sections located between the top (7) and bottom (8).

* * * * *